United States Patent [19]

Stabinsky

[11] Patent Number: 4,751,177
[45] Date of Patent: Jun. 14, 1988

[54] METHODS AND KITS FOR PERFORMING NUCLEIC ACID HYBRIDIZATION ASSAYS

[75] Inventor: Yitzhak Stabinsky, Boulder, Colo.

[73] Assignee: Amgen, Thousand Oaks, Calif.

[21] Appl. No.: 744,509

[22] Filed: Jun. 13, 1985

[51] Int. Cl.[4] .............................................. C12Q 1/68
[52] U.S. Cl. ...................................... 435/6; 435/810; 435/814; 436/501; 436/527; 436/531; 436/808; 436/824; 935/2; 935/3; 935/6; 935/78
[58] Field of Search ............................ 435/6, 810, 814; 436/501, 527, 531, 808, 824; 935/2, 3, 6, 78

[56] References Cited

U.S. PATENT DOCUMENTS

| 4,358,535 | 11/1982 | Falkow et al. | 435/5 |
| 4,415,732 | 11/1983 | Caruthers et al. | 536/27 |
| 4,486,539 | 12/1984 | Ranki et al. | 436/504 |
| 4,522,922 | 6/1985 | Carro et al. | 436/501 X |

FOREIGN PATENT DOCUMENTS

| 0062286 | 10/1982 | European Pat. Off. . |
| 0130515 | 1/1985 | European Pat. Off. . |
| 0153873 | 9/1985 | European Pat. Off. . |
| 84/03520 | 9/1984 | PCT Int'l Appl. . |
| 85/04674 | 10/1985 | PCT Int'l Appl. . |

OTHER PUBLICATIONS

Bornkamm et al., *Curr. Top. Microbiol. Immunol.*, 104, 288–298, (1983).
Dunn et al., *Cell*, 12, 23–36, (1977).
Ranki et al., *Curr. Top. Microbiol. Immunol.*, 104, 307–318, (1983).
Ranki et al., *Gene*, 21, 77–85, (1983).
Wu et al., *Proc. Natl. Acad. Sci.*, (USA), 78, 7059–7063, (1981).

*Primary Examiner*—Sidney Marantz
*Assistant Examiner*—Richard Wagner
*Attorney, Agent, or Firm*—Marshall, O'Toole, Gerstein, Murray & Bicknell

[57] ABSTRACT

A method for the isolation and quantitative detection of a selected single-stranded target polynucleotide from solution. The target polynucleotide is hybridized in solution to a single-stranded mediator polynucleotide, a probe polynucleotide, and an immobilized polynucleotide sequence. The sequence of the mediator polynucleotide comprises a first sequence complementary to a first portion of the target polynucleotide sequence and a second nucleotide sequence complementary to a portion of a single-stranded immobilized polynucleotide sequence. The probe polynucleotide, which carries a detectable label, is complementary to a second portion of the necleotide sequence of the target. The immobilized polynucleotide is immobilized by attachment to a solid support, and, through hybridization to the mediator polynucleotide, functions to immobilize the entire immobilized polynucleotide/target polynucleotide/probe polynucleotide "sandwich".

19 Claims, No Drawings

METHODS AND KITS FOR PERFORMING NUCLEIC ACID HYBRIDIZATION ASSAYS

BACKGROUND

The present invention relates in general to methods and kits for performing nucleic acid hybridization assays and in particular to methods and kits for immobilizing a target nucleic acid on a solid support One characteristic property of nucleic acid, which forms the heritable material of all living organisms, is its ability to form sequence-specific hydrogen bonds with a nucleic acid having a complementary sequence of nucleotides. This ability of nucleic acids to form sequence-specific hydrogen bonds (i.e., to hybridize) with complementary strands of nucleic acid is exploited in techniques generally called hybridization assays.

In a hybridization assay, a nucleic acid having a known sequence is used as a "probe" to search a sample for a "target" complementary sequence. Labelling of the hybrid formed by the probe and the target permits the detection and quantitation of target complementary sequence in the sample.

Because all strains of a particular microorganism share a genetic component in the form of nucleic acids susceptible to diagnosis by means of a hybridization assay, such hybridization assays are valuable research and medical tools. Detection of specific target nucleic acids enables accurate diagnosis of bacterial, fungal and viral disease states in humans, animals and plants. Additionally, the ability to probe for a specific nucleotide sequence is of potential use in the identification and diagnosis of human genetic disorders.

In one type of hybridization assay, called solution hybridization, a labelled probe nucleic acid is added to a solution of a sample to be searched for a target nucleic acid. In order to ensure that both the probe and a target are in a single-stranded state suitable for hybridization, the sample and probe are heated in order to break (denature) the hydrogen bonds which are found between complementary strands of a double-stranded probe or a double-stranded target, or which are found within secondary structure of a probe or target. Upon cooling, the reaction is reversed and double-stranded nucleic acid is allowed to form. The amount of double-stranded nucleic acid which forms may be determined by scintillation counting of the label on the probe after degradation of unhybridized single strands or after isolating double-stranded DNA by passing the hybridization solution over a hydroxyapatite column which selectively retains the double-stranded form. However, if either the probe or the target was introduced in double-stranded form, a reaction reforming (renaturing) double-stranded probe or a double-stranded target competes with the hybridization reaction between probe and target and thereby reduces the sensitivity of this technique.

In another approach to hybridization assays, the renaturation problem is circumvented by immobilizing denatured target nucleic acid on a support. Retention of a labelled probe on a support-bound target after passage of the support-bound target through a solution containing the probe permits detection and quantitation of the target by measurement of the amount of bound label. See, e.g., Falkow, et al., U.S. Pat. No. 4,358,535; and Shafritz, European Patent Application No. A1-0062286. Nevertheless, because the amount of labelled probe is far in excess of the amount of target present, non-specific binding of the labelled probe to the support may swamp the detectable signal from a target present in small amounts.

Still another approach to hybridization assays is called a "sandwich" hybridization. A two-step sandwich hybridization procedure involves the use of an immobilized target nucleic acid which is exposed in a first step to a first nucleic acid probe having a first portion complementary to the target and having a second portion which is not complementary to the target. In a second step, a second, labelled nucleic acid probe, which is complementary to the second portion of the first probe, is allowed to hybridize to the first probe, forming a "sandwich" comprising the first probe between the target and the second probe. Dunn, et al., *Cell*, 12: 23-36 (1977). The sandwich hybridization procedure is relatively easy to perform and is not seriously affected by protein or other biological contaminants. Ranki, et al., *Gene*, 21: 77-85 (1983). However, a two-step sandwich hybridization assay involves considerable delay associated with immobilization of the sample on a filter.

A one-step sandwich assay involves the use of a first nucleic acid probe immobilized on a filter. The first nucleic acid probe is complementary to a first portion of a target nucleic acid. In a single step the filter-bound first probe is exposed to a sample to be searched for the target nucleic acid sequence and to a second, labelled nucleic acid probe complementary to a second portion of the target nucleic acid which portion is separate from (i.e., non-overlapping with) the portion of the target to which the first probe is complementary. Ranki, et al., U.S. Pat. No. 4,486,539. This one-step technique eliminates the delay caused by immobilization of a sample on a filter; eliminates differences between the types of treatment required for binding ribonucleic acid (RNA) and deoxyribonucleic acid (DNA) to certain types of support inasmuch as the first probe may be selected to suit the support; and is even less sensitive to contaminating materials in the sample, e.g., mucus, than is a direct hybridization assay where the target is bound to the support. Ranki, et al., *Curr. Top. Microbiol. Immunol.*, 104: 307-318 (1983). Nevertheless, leakage of the first probe from the support during hybridization occurs frequently and significantly diminishes the sensitivity of the assay. Because hybridization occurs more readily where both partners to the hybridization are in solution rather than where either is bound to a support, the target preferentially binds to leaked first probe. Inasmuch as the amount of leaked first probe is likely to be in excess of the amount of target present, a significant amount of target nucleic acid may be consumed by the leaked probe rather than be bound to the support.

In another approach to hybridization, called blot hybridization, nucleic acids within a sample are separated according to size by electrophoresis through a gel and are transferred to a nitrocellulose filter on which they are immobilized in their relative positions on the gel. Because any target in the sample is confined to a distinct band on the filter, even weak signals resulting from small amounts of target may be distinguished from non-specific background after exposure to a radiolabelled probe. Bornkamm, et al., *Curr. Top. Microbiol. Immunol.*, 104: 288-298 (1983). Nevertheless, the added difficulty and expense of performing an electrophoretic separation on a sample limits the practicality of applying a blot hybridization technique in a clinical setting.

Where a sample is in the form of a touch smear of a fluid, a section through cells, or chromosomal squashes from cells on slides, hybridization may be performed in situ. Generally, a radioactively labelled probe is applied to the sample which is bound to the slide in a histological preparation. After coating the slide with a photographic emulsion, autoradiographic procedures reveal the location of target-probe hybrids by means of clusters of silver grains formed in the emulsion over the hybridization site. However, where only a few grains are observed, it is difficult if not impossible to prove that the hybridization is specific. Bornkamm, et al., supra.

An attempt has been made to improve upon the in situ hybridization technique by using as a label albumin-coated gold spheres which are cross-linked to a nucleic acid having a poly(dT) tail. Chromosomes are hybridized in situ with a probe having a poly(dA) tail which is in turn hybridized to the poly(dT) tail attached to the gold sphere in order to mark the site of hybridization. Wu, et al., *Proc.Natl.Acad.Sci. (USA)*, 78: 7059–7063 (1981). Despite having advantages over other in situ hybridization techniques, this procedure shares a disadvantage with the other in situ hybridization methods in that it requires microscopic examination of large numbers of slides on which is spread only a small amount of sample. As a result, this approach is difficult and time consuming to apply in a clinical setting.

Thus there exists a continuing need in the art for improved nucleic acid hybridization methods for minimizing the effect of probe leakage on the accurate detection of target molecules in a sample.

BRIEF SUMMARY

A method according to the present invention involves searching a sample solution for a selected polynucleotide target. In this method, the sample is exposed to a mediator polynucleotide which has a first portion with a nucleotide sequence complementary to an immobilized polynucleotide and has a second portion, separate and distinct from the first portion, with a nucleotide sequence complementary to a first portion of the target polynucleotide. A probe polynucleotide is introduced to the sample. The probe polynucleotide has an attached reporter group and has a portion with a nucleotide sequence complementary to a second portion of the target polynucleotide which is separate and distinct from the first portion of the target polynucleotide. The target is hybridized with the mediator polynucleotide and with the probe polynucleotide. The mediator polynucleotide is immobilized by hybridization with the immobilized polynucleotide.

A kit according to the present invention is useful for performing a hybridization assay on a sample to search for a selected target polynucleotide. The kit includes a polynucleotide immobilized on a support and a mediator polynucleotide associated with the immobilized polynucleotide. The mediator polynucleotide has a first portion with a nucleotide sequence complementary to the immobilized polynucleotide and has a second portion, separate and distinct from the first portion, with a nucleotide sequence complementary to a first portion of the target. A polynucleotide probe is associated with the immobilized polynucleotide and has a portion with a nucleotide sequence complementary to a second portion of the target polynucleotide. The second portion of the target polynucleotide is separate and distinct from the first portion of the target polynucleotide. A reporter is attached to the probe polynucleotide.

Other aspects and advantages of the present invention will become obvious to one skilled in the art upon consideration of the present invention.

DESCRIPTION OF THE PREFERRED EMBODIMENT

In an examination of the hybridization assay of Ranki, et al., supra, polythymidine (poly T) was synthesized on amine-functionalized controlled pore glass (CPG) (available from Pierce Chemical Company, Rockford, Ill.) and on amine-functionalized Fractosyl-500 glass beads (available from Polysciences, Inc., Warrington, Pa.).

An amine function was attached to F-500 by treating 500 mg of F-500 with a solution of 700 $\mu$l of $H_2N(CH_2)_3Si(OCH_2CH_3)_3$ in 10 ml of 95% ethanol at room temperature for 3 hours. The treated F-500 was washed once with methanol and then once with ethyl ether. The F-500 was dried at room temperature and then baked at 110° C. for 15 hours. It was then washed with water, methanol and water, and then dried. The product was $(F-500)O(CH_2)_3NH_2$, an amine-functionalized F-500.

Next, the amine-functionalized CPG and the amine-functionalized F-500 were prepared for poly T synthesis.

500 mg of the amine-functionalized CPG was reacted for 30 minutes at room temperature with 250 mg (1 millimole) of phthallic anhydride in the presence of 2 ml of anhydrous pyridine and 61 mg of 4-dimethyl amino pyridine to give a product,

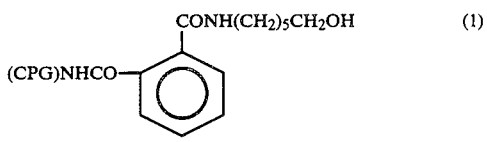

(1)

The product was rinsed with methylene dichloride, ethyl alcohol and ether, and then dried. 450 mg of the product was reacted with 330 mg of dicyclohexylcarbodiimide (DCC) for 30 minutes at room temperature. The solution was decanted and replaced with a solution of 117 mg of 6-amino-1-hexanol in 2 ml of methylene dichloride and then left at room temperature for approximately 8 hours.

Amine-functionalized F-500 was prepared for poly T synthesis by treatment with 400 mg of succinic anhydride and 244 mg of 4-dimethyl aminopyride in 3 ml of anhydrous pyridine for 18 hours at room temperature. The treated F-500 was then washed with N,N-dimethylformamide (DMF), methanol and ethyl ether. A ninhydrin test showed that 98% of the free amino groups had reacted to produce approximately 400 mg of $(F-500)O(CH_2)_3NHCO(CH_2)_2COOH$. This product was suspended in 2 ml of DMF containing 3 millimoles (330 mg) of DCC and 3 millimoles (420 mg) of p-nitrophenol at room temperature overnight. The product,

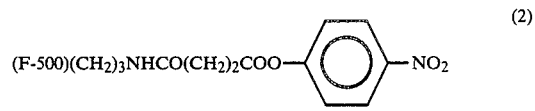

(2)

was washed on a sintered glass funnel with DMF, CH₃CN, CH₂Cl₂ and ethyl ether. A solution of 2 millimoles (234 mg) of H₂N(CH₂)₆OH in 2 ml of DMF was reacted with product (2) overnight. The product of this reaction was a support,

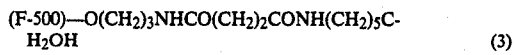

(3)

which was washed with DMF, CH₃CN, methanol and ethyl ether.

The functionalized ester resulting from the preparation of CPG, as outlined above, and product (3) were used as supports for the synthesis of a poly T chain. Each thymidine (T) residue was added as a phosphoramidite according to the procedure of Caruthers, et al., U.S. Pat. No. 4,415,732, in a cycle of phosphoramidite synthesis as described therein.

After 51 cycles of phosphoramidite synthesis for each support, (CPG) p(Tp)₅₀T-OH 5' (hereinafter referred to as CPG-T₅₁) and (F-500) p(Tp)₅₀T-OH 5' (hereinafter referred to as F-500-T₅₁) were respectively obtained A 25 mg unit of each of these two poly T supports was phosphorylated in 100 μl of 1 X ligation buffer [0.05 M Tris, pH 7.4; 0.01 M MgCl₂; 0.01M dithiothreitol (DTT); 1 mM spermidine; 1 mg/ml bovine serum albumin (BSA)]containing 50 nanomoles of ³²P-γ-ATP (specific activity, 300 cpm/picomole) and 6 units of T-4-polynucleotide kinase for 2 hours at 37° C. The supports were then washed with water, 5 X SSPE (0.9M NaCl; 0.06M NaH₂PO₄, pH 7.5; and 5 mM EDTA) at 90° C. The supports were then washed with 90° C. water and dried. The loading of the CPG beads was determined to be 760 picomoles of poly T per milligram and the loading of the F-500 support was determined to be 260 picomoles of poly T per milligram.

For use in hybridization procedures, a single-stranded phage containing the minus (−) or anticoding strand of the Herpes Simplex Virus Type I (HSV-I) glycoprotein D (gD) gene was employed as the target nucleic acid. The entire nucleotide sequence of the double-stranded HSV-I gD gene sequence appears in Table I, the top strand being the plus (+) coding strand and the bottom strand being the anticoding strand. Portions of the plus strand were employed as probe and as a portion of the immobilized nucleotide according to the present invention. These single-stranded sequences have been designated on Table I by the lines drawn above the top, coding strand of the gene.

TABLE I

```
(+) 5'-CTT CAG CGC GAA
(−) 3'-GAA GTC GCG CTT leakage probe
    CGA CCA ACT ACC CCG ATC ATC AGT TAT CCT TAA GGT CTC
    GCT GGT TGA TGG GGC TAG TAG TCA ATA GGA ATT CCA GAG 1
                                      Met Gly Gly Thr Ala Ala Arg
    TTT TCT GTG GTG CGT TCC GGT ATG GGG GGG ACT GCC GCC AGG
    AAA AGA CAC CAC GCA AGG CCA TAC CCC CCC TGA CGG CGG TCC 10                                        20
    Leu Gly Ala Val Ile Leu Phe Val Val Ile Val Gly Leu His
    TTG GGG GCC GTG ATT TTG TTT GTC GTC ATA GTG GGC CTC CAT
    AAC CCC CGG CAC TAA AAC AAA CAG CAG TAT CAC CCG GAG GTA A                             30
    Gly Val Arg Gly Lys Tyr Ala Leu Ala Asp Ala Ser Leu Lys
    GGG GTC CGC GGC AAA TAT GCC TTG GCG GAT GCC TCT CTC AAG
    CCC CAG GCG CCG TTT ATA CGG AAC CGC CTA CGG AGA GAG TTC mediator (part)          40
    Met Ala Asp Pro Asn Arg Phe Arg Gly Lys Asp Leu Pro Val
    ATG GCC GAC CCC AAT CGC TTT CGC GGC AAA GAC CTT CCG GTC
    TAC CGG CTG GGG TTA GCG AAA GCG CCG TTT CTG GAA GGC CAG 50                   probe                    60
    Leu Asp Gln Leu Thr Asp Pro Pro Gly Val Arg Arg Val Tyr
    CTG GAC CAG CTG ACC GAC CCT CCG GGG GTC CGG CGC GTG TAC
    GAC CTG GTC GAC TGG CTG GGA GGC CCC CAG GCC GCG CAC ATG 70
    His Ile Gln Ala Gly Leu Pro Asp Pro Phe Gln Pro Pro Ser
    CAC ATC CAG GCG GGC CTA CCG GAC CCG TTC CAG CCC CCC AGC
    GTG TAG GTC CGC CCG GAT GGC CTG GGC AAG GTC GGG GGG TCG 80                                        90
    Leu Pro Ile Thr Val Tyr Tyr Ala Val Leu Glu Arg Ala Cys
    CTC CCG ATC ACG GTT TAC TAC GCC GTG TTG GAG CGC GCC TGC
    GAG GGC TAG TGC CAA ATG ATG CGG CAC AAC CTC GCG CGG ACG 100
    Arg Ser Val Leu Leu Asn Ala Pro Ser Glu Ala Pro Gln Ile
    CGC AGC GTG CTC CTA AAC GCA CCG TCG GAG GCC CCC CAG ATT
    GCG TCG CAC GAG GAT TTG CGT GGC AGC CTC CGG GGG GTC TAA 110
    Val Arg Gly Ala Ser Glu Asp Val Arg Lys Gln Pro Tyr Asn
    GTC CGC GGG GCC TCC GAA GAC GTC CGG AAA CAA CCC TAC AAC
    CAG GCG CCC CGG AGG CTT CTG CAG GCC TTT GTT GGG ATG TTG
```

TABLE I-continued

```
                 120                                                130
Leu  Thr  Ile  Ala  Trp  Phe  Arg  Met  Gly  Gly  Asn  Cys  Ala  Ile
CTG  ACC  ATC  GCT  TGG  TTT  CGG  ATG  GGA  GGC  AAC  TGT  GCT  ATC
GAC  TGG  TAG  CGA  ACC  AAA  GCC  TAC  CCT  CCG  TTG  ACA  CGA  TAG

140
Pro  Ile  Thr  Val  Met  Glu  Tyr  Thr  Glu  Cys  Ser  Tyr  Asn  Lys
CCC  ATC  ACG  GTC  ATG  GAG  TAC  ACC  GAA  TGC  TCC  TAC  AAC  AAG
GGG  TAG  TGC  CAG  TAC  CTC  ATG  TGG  CTT  ACG  AGG  ATG  TTG  TTC 150                                      160
Ser  Leu  Gly  Ala  Cys  Pro  Ile  Arg  Thr  Gln  Pro  Arg  Trp  Asn
TCT  CTG  GGG  GCC  TGT  CCC  ATC  CGA  ACG  CAG  CCC  CGC  TGG  AAC
AGA  GAC  CCC  CGG  ACA  GGG  TAG  GCT  TGC  GTC  GGG  GCG  ACC  TTG

170
Tyr  Tyr  Asp  Ser  Phe  Ser  Ala  Val  Ser  Glu  Asp  Asn  Leu  Gly
TAC  TAT  GAC  AGC  TTC  AGC  GCC  GTC  AGC  GAG  GAT  AAC  CTG  GGG
ATG  ATA  CTG  TCG  AAG  TCG  CGG  CAG  TCG  CTC  CTA  TTG  GAC  CCC

180
Phe  Leu  Met  His  Ala  Pro  Ala  Phe  Glu  Thr  Ala  Gly  Thr  Tyr
TTC  CTG  ATG  CAC  GCC  CCC  GCG  TTT  GAG  ACC  GCC  GGC  ACG  TAC
AAG  GAC  TAC  GTG  CGG  GGG  CGC  AAA  CTC  TGG  CGG  CCG  TGC  ATG 190                                            200
Leu  Arg  Leu  Val  Lys  Ile  Asn  Asp  Trp  Thr  Glu  Ile  Thr  Gln
CTG  CGG  CTC  GTG  AAG  ATA  AAC  GAC  TGG  ACG  GAG  ATT  ACA  CAG
GAC  GCC  GAG  CAC  TTC  TAT  TTG  CTG  ACC  TGC  CTC  TAA  TGT  GTC

210
Phe  Ile  Leu  Glu  His  Arg  Ala  Lys  Gly  Ser  Cys  Lys  Tyr  Ala
TTT  ATC  CTG  GAG  CAC  CGA  GCC  AAG  GGC  TCC  TGT  AAG  TAC  GCC
AAA  TAG  GAC  CTC  GTG  GCT  CGG  TTC  CCG  AGG  ACA  TTC  ATG  CGG 220                                           230
Leu  Pro  Leu  Arg  Ile  Pro  Pro  Ser  Ala  Cys  Leu  Ser  Pro  Gln
CTC  CCG  CTG  CGC  ATC  CCC  CCG  TCA  GCC  TGC  CTC  TCC  CCC  CAG
GAG  GGC  GAC  GCG  TAG  GGG  GGC  AGT  CGG  ACG  GAG  AGG  GGG  GTC

240
Ala  Tyr  Gln  Gln  Gly  Val  Thr  Val  Asp  Ser  Ile  Gly  Met  Leu
GCC  TAC  CAG  CAG  GGG  GTG  ACG  GTG  GAC  AGC  ATC  GGG  ATG  CTG
CGG  ATG  GTC  GTC  CCC  CAC  TGC  CAC  CTG  TCG  TAG  CCC  TAC  GAC

250
Pro  Arg  Phe  Ile  Pro  Glu  Asn  Gln  Arg  Thr  Val  Ala  Val  Tyr
CCC  CGC  TTC  ATC  CCC  GAG  AAC  CAG  CGC  ACC  GTC  GCC  GTA  TAC
GGG  GCG  AAG  TAG  GGG  CTC  TTG  GTC  GCG  TGG  CAG  CGG  CAT  ATG 260                                            270
Ser  Leu  Lys  Ile  Ala  Gly  Trp  His  Gly  Pro  Lys  Ala  Pro  Tyr
AGC  TTG  AAG  ATC  GCC  GGG  TGG  CAC  GGG  CCC  AAG  GCC  CCA  TAC
TCG  AAC  TTC  TAG  CGG  CCC  ACC  GTG  CCC  GGG  TTC  CGG  GGT  ATG

280
Thr  Ser  Thr  Leu  Leu  Pro  Pro  Glu  Leu  Ser  Glu  Thr  Pro  Asn
ACG  AGC  ACC  CTG  CTG  CCC  GCG  GAG  CTG  TCC  GAG  ACC  CCC  AAC
TGC  TCG  TGG  GAC  GAC  GGG  CGC  CTC  GAC  AGG  CTC  TGG  GGG  TTG 290                                           300
Ala  Thr  Gln  Pro  Glu  Leu  Ala  Pro  Glu  Asp  Pro  Glu  Asp  Ser
GCC  ACG  CAG  CCA  GAA  CTC  GCC  CCG  GAA  GAC  CCC  GAG  GAT  TCG
CGG  TGC  GTC  GGT  CTT  GAG  CGG  GGC  CTT  CTG  GGG  CTC  CTA  AGC

310
Ala  Leu  Leu  Glu  Asp  Pro  Val  Gly  Thr  Val  Ala  Pro  Gln  Ile
GCC  CTC  TTG  GAG  GAC  CCC  GTG  GGG  ACG  GTG  GCG  CCG  CAA  ATC
CGG  GAG  AAC  CTC  CTG  GGG  CAC  CCC  TGC  CAC  CGC  GGC  GTT  TAG

320
Pro  Pro  Asn  Trp  His  Ile  Pro  Ser  Ile  Gln  Asp  Ala  Ala  Thr
CCA  CCA  AAC  TGG  CAC  ATC  CCG  TCG  ATC  CAG  GAC  GCC  GCG  ACG
GGT  GGT  TTG  ACC  GTG  TAG  GGC  AGC  TAG  GTC  CTG  CGG  CGC  TGC 330                                       340
Pro  Tyr  His  Pro  Pro  Ala  Thr  Pro  Asn  Asn  Met  Gly  Leu  Ile
CCT  TAC  CAT  CCC  CCG  GCC  ACC  CCG  AAC  AAC  ATG  GGC  CTG  ATC
GGA  ATG  GTA  GGG  GGC  CGG  TGG  GGC  TTG  TTG  TAC  CCG  GAC  TAG
```

TABLE I-continued

```
                              350
Ala Gly Ala Val Gly Gly Ser Leu Leu Ala Ala Leu Val Ile
GCC GGC GCG GTG GGC GGC AGT CTC CTG GCA GCC CTG GTC ATT
CGG CCG CGC CAC CCG CCG TCA GAG GAC CGT CGG GAC CAG TAA 360                                     370
Cys Gly Ile Val Tyr Trp Met His Arg Arg Thr Arg Lys Ala
TGC GGA ATT GTG TAC TGG ATG CAC CGC CGC ACT CGG AAA GCC
ACG CCT TAA CAC ATG ACC TAC GTG GCG GCG TGA GCC TTT CGG

380
Pro Lys Arg Ile Arg Leu Pro His Ile Arg Glu Asp Asp Gln
CCA AAG CGC ATA CGC CTC CCC CAC ATC CGG GAA GAC GAC CAG
GGT TTC GCG TAT GCG GAG GGG GTG TAG GCC CTT CTG CTG GTC

390
Pro Ser Ser His Gln Pro Leu Phe Tyr ***
CCG TCC TCG CAC CAG CCC TTG TTT TAC TAG ATA CCC CCC CTT
GGC AGG AGC GTG GTC GGG AAC AAA ATG ATC TAT GGG GGG GAA

AAT GGG TGC GGG GGG GTC AGG TCT GCG GGG TTG GGA TGG GAC
TTA CCC ACG CCC CCC CAG TCC AGA CGC CCC AAC CCT ACC CTG

CTT AAC TCC ATA TAA AGC GAG TCT GGA AGG GGG GAA AGG CGG
TTA CCC ACG CCC CCC CAG TCC AGA CGC CCC AAC CCT ACC CTG

ACA GTC GAT AAG TCG GTA GCG GGG GAC GCG CAC CTG TTC CGC
TGT CAG CTA TTC AGC CAT CGC CCC CTG CGC GTG GAC AAG GCG

CTG TCG CAC CCA CAG CTT TTT CGC GAA CCG TCC CGT TTT CGG
GAC AGC GTG GGT GTC GAA AAA GCG CTT GGC AGG GCA AAA GCC

GAT-3'
CTA-5'
```

Four synthetic polynucleotides were synthesized using the techniques of Caruethers, et al., supra, and were hybridized and ligated in 1 X ligation buffer containing 7 nM ATP and 4.5 units of T-4 ligase to form and counted on a scintillation counter. The results appear in Table II.

TABLE II

```
(+) 5'-CTT CAG CGC GAA CGA CCA ACT ACC CCG ATC      (4)
    GAA GTC GCG CTT GCT GGT TGA TGG GGC TAG

ATC AGT TAT CCT TAA GGT CTC
    TAG TCA ATA GGA ATT CCA GAG AAAAA-5' (−)
```

The poly A 5' end of the (−) strand of double-stranded polynucleotide (4) (approximately 250 picomoles) was incubated overnight in ligation buffer containing 7 mM ATP and 4.5 units of T-4 DNA ligase. The supports were then washed three times with 100 μl of ligation buffer, three times with 100 μl of water at room temperature, and three times with 100 μl of water at 90° C. Thus, the (+) strand of polynucleotide (4) was ligated to each of the supports CPG-T$_{51}$ and F-500-T$_{51}$, while the (−) strand of polynucleotide (4) was removed by denaturation in the course of the washings at 90° C. to leave a complex (denoted as CPG-T$_{51\text{-}51}$ and F-500-T$_{51\text{-}51}$) having the (+) strand of polynucleotide (4) as an immobilized probe.

A hybridization solution was prepared containing 12.5 μl of 20 X SSPE; 0.5 picomoles of HCl-cut pHgD 2.9 (a plasmid-containing 2.9 kilobase insert of HSV-I plus 2.7 kilobases of plasmid sequence) in 13.6 μl; 1 picomole of $^{32}$P-labelled probe A (labelled by phosphorylation with $^{32}$P-γ-ATP according to the procedure described above for T$_{51}$) in 10 μl; 1.0 μl of 10% sodium dodecyl sulfate (SDS); and 9.9 μl of H$_2$O. The hybridization solution was boiled for 5 minutes and then incubated at 60° C. Samples were taken at 15 minutes, 30 minutes, 60 minutes, and 7 hours after boiling, washed three times at room temperature in 5 X SSPE,

| Time | Control | Hybrid | Corrected CPM |
|---|---|---|---|
| 15 minutes | 93,800 | 86,100 | −7,700 |
| 30 minutes | 92,700 | 86,000 | −6,700 |
| 60 minutes | 95,100 | 84,320 | −10,800 |
| . | | | |
| . | | | |
| 7 hours | 98,400 | 77,800 | −20,600 |

As indicated in Table II, the control (unhybridized CPG-T$_{51\text{-}51*}$) produced a higher level of counts than did the hybrid (CPG-T$_{51*\text{-}51}$ hybridized with pHGd 2.9 and probe A*), suggesting that the immobilized poly T separated from the bead.

In order to localize the point of separation from the bead, the leakage probe was 5' $^{32}$P-labelled, as described above, and attached to a labelled CPG-T$_{51}$ support to produce CPG-T$_{51*\text{-}51*}$. The 5' $^{32}$P-label was removed from a portion of the CPG-T$_{51*\text{-}51*}$ by phosphatase treatment to produce CPG-T$_{51*\text{-}51}$. Samples of these two immobilized, labelled polynucleotides were counted and then boiled in 500 μl of 5 X SSPE for periods of 15 minutes, 30 minutes, 45 minutes and 75 minutes to obtain the results illustrated in Table III.

TABLE III

|  | CPG-T$_{51*\text{-}51*}$ | Loss | CPG-T$_{51*\text{-}51}$ (Phosphatased) | Loss |
|---|---|---|---|---|
| Start (CPM) | 96,800 |  | 9,711 |  |
| Boil 15 min | 70,426 | 27% | 6,900 | 29% |
| 30 min | 40,716 | 42% | 5,241 | 24% |
| 45 min | 28,940 | 29% | 3,568 | 31% |
| 75 min | 14,375 | 50% | 2,247 | 37% |

Comparison of the two columns in Table III indicates that dramatic leakage occurs whether only T$_{51}$ is labelled or whether both T$_{51}$ and the leakage probe are labelled, so that separation from the support apparently occurs at the point of attachment to the CPG.

Similar experiments were run on an aliphatic amide linkage of T$_{51}$ to F-500. These experiments indicated that support by an aliphatic amine linkage resulted in two to three times slower leakage than the aromatic amine linkage examined in Tables II and III. Specifically, CPG attached to T$_{51}$ by an aromatic amine linkage showed 20% leakage at 65% C. after three hours, while F-500 linked to T$_{51}$ by an aliphatic amine linkage displayed only 7.8% leakage at 65° C. after three hours.

A different sort of linkage system, wherein poly T was directly synthesized on F-500, was examined for leakage. In this system, 500 mg of glass beads (available from Polysciences, Inc., Warrington, Pa., as Catalog No. 5483) were exposed to 2 ml of 0.5 molar tetrazole and 0.5 molar T-phosphoramidites for 2 hours in anhydrous CH$_3$CN, and then washed with CH$_3$CN and treated with an iodine solution for 5 minutes. Thereafter, phosphoramidite synthesis according to Caruthers, et al., supra, was used to obtain F-500-T$_{25}$, which was $^{32}$P-labelled The system was examined for leakage as above, with the result that after 3 hours at 65° C. in 500 μl of 5 X SSPE, only 0.5% of the poly T leaked from the support.

These results have significant implications for the practicality of one-step sandwich assays according to Ranki, et al., supra. In such assays, an immobilized single strand of DNA is attached to a solid support. A single-stranded DNA target is immobilized by hybridization to the strand attached to the support. A labelled probe is then hybridized with the target to permit detection of the immobilized strand-target-probe sandwich.

In order for such a single-step model to be practical, it is necessary: that the immobilized strand exhibit high loading to the support (1 to 5 picomoles of DNA per assay mixture, assuming that detection of as low as 10$^6$ target molecules is desired); and that no leakage of DNA from the support occur.

Assuming 0.05% leakage of 3×10$^{12}$ molecules (5 picomoles) of an immobilized strand, 1.5×10$^9$ molecules of immobilized strand are leaked into the hybridization medium. If the number of target molecules to be detected is 3×10$^6$ and, as may be shown, the efficiency of hybridization between the immobilized strand and the target is an order of magnitude lower than the efficiency of hybridization between the leaked strand and the target, 75% of the target molecules hybridize with leaked strands rather than immobilized strands, causing a loss of ¾ of the potential signal.

Inasmuch as the lowest amount of leakage actually measured was 10 times this assumed figure (i.e., 0.5%), it is likely that more than 96% of the potential signal is lost. Therefore, there is a need for some means for preventing the leaked strands from drastically reducing the detection efficiency of the target.

In the method according to the present invention, a single-stranded polynucleotide is immobilized on a solid support. The immobilized polynucleotide is hybridized with a first portion of a single-stranded mediator polynucleotide. A second portion of the mediator polynucleotide is hybridized with a first portion of a single-stranded target polynucleotide, thereby immobilizing it. Of course, the first and second portions of the nucleotide sequence of the mediator are preferably separate and distinct (i.e., non-overlapping) in order to prevent mutual interference. The target polynucleotide is made detectable by hybridization at a second portion to a probe polynucleotide attached to a reporter group. The first and second portions of the nucleotide sequence are preferably separate and distinct (i.e., non-overlapping) in order to prevent mutual interference.

Conventional methods may be used to detect or quantify the target by measuring the amount of label on the immobilized "sandwich" hybrid and may also involve separating the immobilized hybrid from the solution. The detectable label may be radioactive, such as $^{125}$I, $^{35}$P, and the like, or non-radioactive (e.g., fluorescent or immunological).

The method of the present invention may be employed where the target polynucleotide is a deoxyribonucleic or ribonucleic acid. In either case, depending on preference for a DNA-DNA, RNA-RNA, or DNA-RNA hybridization between immobilized polynucleotide, labelled probe polynucleotide, mediator and target, the mediator and probe polynucleotides may be deoxyribonucleic or ribonucleic acids.

Any solid support to which a sequence may be bound is useful in this method, including both porous and non-porous supports, e.g., such as silica gel, controlled pore glass, and nitrocellulose paper. Most commercially available supports contain or may be provided with amine or carboxylic acid functional groups to which DNA may be linked. Alternatively, a bead coating having multiple points of attachment for immobilizing a polynucleotide to the support may be employed.

One immobilized polynucleotide for use according to the present invention is a poly-thymidine strand which may be synthesized on a support, as described above, without the need for deprotection at the end of the synthesis. The complementary mediator polynucleotide may be poly-adenosine. Where poly T/poly A hybridization is employed, the hybridization assay for the target polynucleotide is preferably conducted at a temperature lower than the melting point of AT pairs to prevent the immobilized polynucleotide from disengaging from the mediator.

The use of a huge excess of mediator polynucleotide sequence minimizes the inaccuracies present in sandwich assays of the prior art. Leakage of immobilized polynucleotide from the support, a major defect in presently available sandwich assays, does not affect the accuracy of the present method because the immobilized polynucleotide is not complementary to the target polynucleotide. Use of excess amounts (i.e., in great excess of the anticipated amount of leaked immobilized probe) of the mediator polynucleotide will "buffer" any "immobilized" polynucleotide which leaks into solution by binding to the leaked polynucleotide. This prevents withdrawal of target polynucleotide upon washing of the support after hybridization. Thus the method of the present invention provides greatly increased sensitivity (approximately 90% efficiency) in detecting small amounts of target polynucleotide.

The following examples illustrate the practice of the method according to the present invention. Specifically, hybridization assays are demonstrated which employ the mediator system according to the present invention to detect and to quantitate the amount of desired target sequence in a solution.

Example 1 describes a hybridization assay according to the method of the present invention.

EXAMPLE 1

A chain of fifty-three thymidine bases (poly-T chain) was synthesized on a solid support, as described above, for use as the immobilized polynucleotide according to the present invention. Both F-500 and CPG were employed as the supports. The loading of the poly-T chains on the supports was determined by the demethoxytrityl assay as follows:

$$\text{Loading } \mu\text{moles/gram} = \frac{A_{498} \times \text{dilution}}{\text{mg bead}} \times 14.3$$

wherein $A_{498}$ is the absorbence of the solution containing the removed demethoxytrityl components at 498 nm. CPG-$T_{53}$ was found to be loaded at 3.6 nanomoles/mg, while Fractosyl-$T_{53}$ was loaded at 2.8 nanomoles/mg.

In the assay, 10 picomoles of probe polynucleotide were phosphorylated using $^{32}$P-labelled adenosine triphosphate, resulting in a specific activity of approximately $6 \times 10^6$ cpm/picomole. Table IV sets forth the experimental protocol and the results of the hybridization experiment. To each of nine assay tubes was added 1.5 mg of either CPG-$T_{53}$ or F-500-$T_{53}$. The reaction buffer employed was 6X SSPE and the final volume in each tube was 25 μl. No foreign DNA was added. In the first step of the assay, the target (Φ2, a single-stranded bacteriophage containing 1.3 kilobases of HSV-I including the sequence set forth in Table I) was hybridized at 45° C. with either the labelled probe polynucleotide (having the sequence set forth in Table I) and the mediator polynucleotide (having the sequence as indicated in Table I, but having a 27-nucleotide poly A tail at the 5' end), the probe polynucleotide alone, or mediator polynucleotide alone for 90 minutes. This hybridization mixture was thereafter reacted with the support system at 45° C. for 30 or 60 minutes. After both hybridization steps were completed, each tube was washed three times with buffer at room temperature and the immobilized and labelled target sandwich on the bead counted using a scintillation counter.

target to mediator, the greater the immobilizing efficiency.

The following example illustrates modification of the assay procedures to decrease non-specific DNA binding and provide a lower load capacity on the support.

EXAMPLE 2

Poly T was synthesized on untreated glass beads (GB) as above in 66 cycles and detritylated to obtain GB-$T_{66}$ having a loading of 12 picomoles/mg.

In order to determine the loading of poly-T accessible for hybridization to the mediator polynucleotide sequence, 50 picomoles of the mediator polynucleotide of Example 1 were phosphorylated with $^{32}$P to a specific activity of 30,000 cpm/mole following the procedure of Example 1. 50 picomoles of the probe polynucleotide of Example 1 were similarly labelled to the same specific activity.

Table V indicates the protocol of the experiment conducted to ascertain appropriate loading conditions for the assay. The beads with attached immobilized probe were incubated in the presence of labelled mediator polynucleotide or target probe at 45° C. for 2 hours in 6X SSPE buffer, washed 3 times at room temperature with buffer, and counted.

TABLE V

| Tube | Mediator | Probe | GB-$T_{66}$ | CPM | Loading |
|---|---|---|---|---|---|
| 1 | $1.2 \times 10^6$ cpm | — | 2 mg | 114,500 | 1.9 pmoles per mg |
| 2 | $1.2 \times 10^6$ cpm | — | 5 mg | 268,500 | 1.79 pmoles per mg |
| 3 | — | $1.2 \times 10^6$ cpm | 5 mg | 2,200 | — |

The results, as shown in Table V, indicate that the loading of the accessible poly-T chain is approximately 1.84 picomoles/mg and that the non-specific binding is less than 1% under the conditions of the assay.

The following example illustrates the sensitivity of a hybridization assay according to the method of the present invention.

EXAMPLE 3

In the first step of the assay, various amounts of the target of Example 1 were hybridized at 48° C. with 0.9 picomoles of the $^{32}$P-labelled polynucleotide probe of Example 1 (specific activity $4 \times 10^6$ cpm/picomole), 1 picomole of the mediator polynucleotide of Example 1, and 5 μg of human placental DNA (HP-DNA) (available from Sigma Chemical Company, St. Louis, Mo.) for 100 minutes. The final volume of each tube was 25 μl, employing 6X SSPE as buffer. Each resulting hy-

TABLE IV

| Tube | Target | Probe | Mediator | Support | Reaction Time | CPM | CPM Minus Background | CPM/fMol | Percent Efficiency |
|---|---|---|---|---|---|---|---|---|---|
| 1 | 250 fmol | 1 pmol | 10 pmol | F-$T_{53}$ | 30 min | 255,000 | 245,160 | 980 | 16.3 |
| 2 | 250 fmol | 1 pmol | 10 pmol | F-$T_{53}$ | 60 min | 432,000 | 422,160 | 1688 | 28.3 |
| 3 | 250 fmol | 1 pmol | 10 pmol | CPG-$T_{53}$ | 30 min | 276,640 | 265,840 | 1063 | 17.7 |
| 4 | 250 fmol | 1 pmol | 10 pmol | CPG-$T_{53}$ | 60 min | 466,000 | 455,200 | 1820 | 30.3 |
| 5 | 250 fmol | 1 pmol | None | F-$T_{53}$ | 30 min | 9,840 | — | — | — |
| 6 | 250 fmol | 1 pmol | None | CPG-$T_{53}$ | 30 min | 10,800 | — | — | — |
| 7 | 50 fmol | 1 pmol | 10 pmol | CPG-$T_{53}$ | 60 min | 106,900 | 97,100 | 1942 | 32.3 |
| 8 | 50 fmol | 1 pmol | 10 pmol | F-$T_{53}$ | 60 min | 130,000 | 120,000 | 2400 | 40.0 |
| 9 | None | 1 pmol | None | F-$T_{53}$ | — | 5,800 | — | — | — |

The results in Table IV indicate that hybridized probe polynucleotide/mediator polynucleotide is capable of immobilizing the target polynucleotide, and that the longer the reaction time and the smaller the ratio of brid was thereafter reacted with 5 mg of the GB-$T_{66}$ of Example 2 for 100 minutes at 39° C. The beads were then separated from solution, washed 3 times with buffer at room temperature, and the amount of immobilized, labelled sandwich was counted. Table VI below sets forth the results.

TABLE VI

| Tube | Target | CPM | CPM Minus Background | Efficiency |
|---|---|---|---|---|
| 1 | 16 fmol | 42,150 | 38,000 | 59% |
| 2 | 4 fmol | 13,900 | 9,750 | 61% |
| 3 | 1 fmol | 8,600 | 4,450 | 111% |
| 4 | 0.5 fmol | 6,650 | 2,500 | 125% |
| 5 | 0.25 fmol | 5,200 | 1,050 | 105% |
| 6 | 0.00 fmol | — | — | — |

These results demonstrate the sensitivity of the probe/mediator "sandwich" assay of the present invention in detecting target concentrations of 1 femtomole or less. It is expected that better sensitivity could be achieved through use of different detection systems, e.g., antigenic systems, or other non-isotopic systems.

It is expected that numerous modifications and variations will occur to those skilled in the art upon consideration of the present invention. For example, it is obvious to one skilled in the art that the component elements necessary to test a sample for the presence of a particular target polynucleotide may be assembled in advance in the form of a kit. Specifically, a mediator polynucleotide, a probe polynucleotide bound to a reporter group and complementary to a separate and distinct, different portion of the target polynucleotide than the first probe, and an immobilized polynucleotide bound to a support may be associated in such a kit as separately packaged components. Such a kit may be used to detect the presence of and to quantify the target for which it was designed by combining the probes and support with a sample to be tested for a target polynucleotide prepared, according to the procedure of Ranki, et al., *Curr.Top. Microbiol.Immunol.*, 104: 317–318 (1983). Consequently, it is intended that the present invention be given the full scope of the appended claims.

What is claimed is:

1. A method for searching a sample solution for selected target polynucleotide suspended in the solution comprising the steps of:
   (a) exposing the sample to a mediator polynucleotide having a first portion with a nucleotide sequence complementary to and hybridizable with an immobilized polynucleotide and having a second portion, separate and distinct from the first portion, with a nucleotide sequence complementary to and hybridizable with a first portion of the target polynucleotide;
   (b) introducing to the sample a probe polynucleotide having an attached reporter group and having a portion with a nuceotide sequence complementary to and hybridizable with a second portion of the target polynucleotide, said second portion being separate and distinct from said first portion of the target polynucleotide;
   (c) hybridizing the first portion of the target with the second portion of the mediator polynucleotide and the second portion of the target polynucleotide with the portion of the probe polynucleotide; and
   (d) immobilizing the mediator polynucleotide by hybridization of the first portion of the mediator polynucleotide with the immobilized polynucleotide.

2. The method as recited in claim 1 further comprising the step of qualitating the amount of signal supplied by said detectable label on said immobilized hybrid product.

3. The method as recited in claim 1 wherein said target polynucleotide is a polydeoxyribonucleotide.

4. The method as recited in claim 1 wherein said target polynucleotide is a polyribonucleotide.

5. The method as recited in claim 3 or 4 wherein said mediator polynucleotide sequence is a deoxyribonucleic acid sequence.

6. The method as recited in claim 3 or 4 wherein said mediator polynucleotide sequence is ribonucleic acid sequence.

7. The method as recited in claim 3 or 4 wherein said probe polynucleotide sequence is a deoxyribonucleic acid sequence.

8. The method as recited in claim 3 or 4 wherein said probe polynucleotide sequence is a ribonucleic acid sequence.

9. The method as recited in claim 3 or 4 wherein said immobilized polynucleotide is a polydeoxyribonucleotide.

10. The method as recited in claim 3 or 4 wherein said immobilized nucleotide is a polyribonucleotide.

11. A kit for performing a hybridization assay on a sample to search for a selected target polynucleotide comprising:
    a polynucleotide immobilized on a support;
    a mediator polynucleotide, associated as a component of a kit with said immobilized polynucleotide, having a first portion with a nucleotide sequence complementary to and hybridizable with said immobilized polynucleotide and having a second portion, separate and distinct from the first portion, with a nucleotide sequence complementary to and hybridizable with a first portion of the target polynucleotide;
    a polynucleotide probe, associated as a component of a kit with said immobilized polynucletide, having a portion with a nucleotide sequence complementary to and hybridizable with a second portion of the target polynucleotide, said second portion being separate and distinct from said first portion of the target polynucleotide; and
    a reporter attached to said probe polynucleotide.

12. The kit as recited in claim 11 wherein said target polynucleotide is a polydeoxyribonucleotide.

13. The kit as recited in claim 11 wherein said target polynucleotide is a polyribonucleotide.

14. The kit as recited in claim 12 or 13 wherein said mediator polynucleotide sequence is a deoxyribonucleic acid sequence.

15. The kit as recited in claim 12 or 13 wherein said mediator polynucleotide sequence is a ribonucleic acid sequence.

16. The kit as recited in claim 12 or 13 wherein said probe polynucleotide sequence is a deoxyribonucleic acid sequence.

17. The kit as recited in claim 12 or 13 wherein said probe polynucleotide sequence is a ribonucleic acid sequence.

18. The kit as recited in claim 12 or 13 wherein said immobilized polynucleotide is a polydeoxyribonucleotide.

19. The kit as recited in claim 12 or 13 wherein said immobilized polynucleotide is a polyribonucleotide.

* * * * *

UNITED STATES PATENT AND TRADEMARK OFFICE
CERTIFICATE OF CORRECTION

PATENT NO. : 4,751,177

DATED : June 14, 1988

INVENTOR(S) : Yitzhak Stabinsky

It is certified that error appears in the above-identified patent and that said Letters Patent is hereby corrected as shown below: On the title page:

In the abstract at line 13 please delete "necleotide" and insert -- nucleotide -- therefor; and At line 17 please delete "-".

In the Specification at column 2, line 16 please put -- cell -- in italics;

At column 2, line 19 please put -- Gene -- in italics;

At column 3, lines 4, and 5 please put -- in situ -- in italics;

At column 3, line 13 please put -- supra -- in italics;

At column 3, line 18 please put -- in situ -- in italics;

At column 3, line 22 please put -- in situ -- in italics;

At column 3, line 24 please put -- in situ -- in italics;

At column 4, line 10 please put -- supra -- in italics;

At column 5, line 22 please insert a period after -- obtained --;

At column 5, line 25 please delete "0.01n" and insert -- 0.01 M -- therefor;

At column 6, line 2 please delete ")containing" and insert -- ) containing -- therefor;

At column 6, line 6 please delete "0.9m" and insert -- 0.9 M -- therefor;

At column 6, line 6 please delete "0.6m" and insert -- 0.6 M -- therefor;

At column 9, line 33 please put -- supra -- in italics;

At column 9, line 35 please delete "7nm" and insert -- 7 mM -- therefor;

At column 11, line 22 please delete "65%C." and insert -- 65°C -- therefor;

At column 11, line 24 please delete "65°C." and insert -- 65°C -- therefor

At column 11, line 34 please put "supra" in italics;

At column 11, line 35 please insert a period after -- labelled --;

At column 11, line 36 please delete "65°C." and insert -- 65°C -- therefor;

At column 11, line 41 please put -- supra -- in italics;

At column 13, line 41 please delete "45°C." and insert -- 45°C -- therefore;

UNITED STATES PATENT AND TRADEMARK OFFICE
CERTIFICATE OF CORRECTION

PATENT NO. : 4,751,177

DATED : June 14, 1988

INVENTOR(S) : Yitzhak Stabinsky

It is certified that error appears in the above-identified patent and that said Letters Patent is hereby corrected as shown below:

at Column 13, line 48 please delete "45°C." and insert -- 45°C -- therefor;

at Column 14, line 23 please delete "45°C." and insert -- 45°C -- therefor;

at Column 14, line 45 please delete "48°C." and insert -- 48°C -- therefor;

at Column 14, line 68 please delete "39°C." and insert -- 39°C -- therefor;

In the Claims at Column 15, line 58 please delete "nuceotide" and insert -- nucleotide -- therefor;

at Column 15, line 63 please delete "ofthe" and insert -- of the -- therefor;

at Column 16, line 2 please delete "qualitating" and insert -- quantitating -- therefor;

at Column 16, line 13 please delete "is ribonucleic" and insert -- is a ribonucleic -- therefor; and at Column 16, line 40 please delete "polyncletide" and insert -- polynucleotide -- therefor.

Signed and Sealed this

Seventeenth Day of July, 1990

*Attest:*

HARRY F. MANBECK, JR.

*Attesting Officer*    *Commissioner of Patents and Trademarks*